US008652999B1

(12) United States Patent
Satchivi et al.

(10) Patent No.: US 8,652,999 B1
(45) Date of Patent: Feb. 18, 2014

(54) HERBICIDAL COMPOSITIONS COMPRISING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND A SULFONYLAMINO CARBONYLTRIAZOLINONE

(71) Applicants: Norbert M. Satchivi, Carmel, IN (US); Bryston L. Bangel, Camby, IN (US)

(72) Inventors: Norbert M. Satchivi, Carmel, IN (US); Bryston L. Bangel, Camby, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/786,758

(22) Filed: Mar. 6, 2013

Related U.S. Application Data

(60) Provisional application No. 61/674,995, filed on Jul. 24, 2012.

(51) Int. Cl.
*A01N 43/40* (2006.01)
(52) U.S. Cl.
USPC .......................................................... 504/130

(58) Field of Classification Search
None
See application file for complete search history.

(56) References Cited

U.S. PATENT DOCUMENTS 7,314,849 B2 * 1/2008 Balko et al. .................. 504/244

* cited by examiner

*Primary Examiner* — Alton Pryor
(74) *Attorney, Agent, or Firm* — Michael R. Asam

(57) ABSTRACT

A herbicidal composition containing (a) a compound of formula (I):

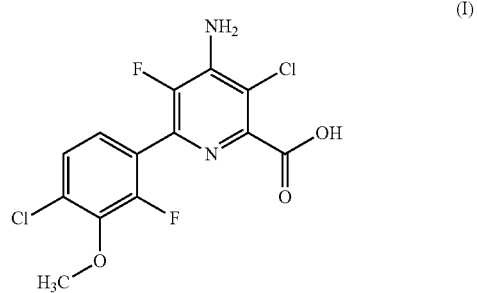

or an agriculturally acceptable salt or ester thereof and (b) a sulfonylaminocarbonyltriazone herbicide, or an agriculturally acceptable salt or ester thereof.

13 Claims, No Drawings

HERBICIDAL COMPOSITIONS COMPRISING 4-AMINO-3-CHLORO-5-FLUORO-6-(4-CHLORO-2-FLUORO-3-METHOXYPHENYL)PYRIDINE-2-CARBOXYLIC ACID OR A DERIVATIVE THEREOF AND A SULFONYLAMINOCARBONYLTRIAZOLINONE

This application claims the benefit of U.S. Provisional Patent Application Ser. No. 61/674,995, filed Jul. 24, 2012.

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use.

SUMMARY

Provided herein are herbicidal compositions comprising a herbicidally effective amount of (a) a compound of the formula (I)

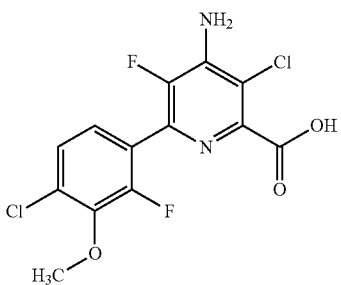

or an agriculturally acceptable salt or ester of thereof, and (b) a sulfonylaminocarbonyltriazone herbicide, or an agriculturally acceptable salt or ester thereof. The compositions may also contain an agriculturally acceptable adjuvant or carrier.

Provided herein also are methods of controlling undesirable vegetation comprising applying (a) a compound of formula (I) or an agriculturally acceptable ester or salt thereof and (b) a sulfonylaminocarbonyltriazone herbicide, or an agriculturally acceptable salt or ester thereof.

DETAILED DESCRIPTION

Definitions

As used herein, the compound of formula (I) has the following structure:

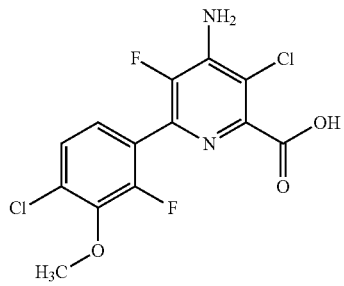

The compound of formula (I) can be identified by the name 4-amino-3-chloro-6-(4-chloro-2-fluoro-3-methoxyphenyl)-5-fluoropyridine-2-carboxylic acid and has been described in U.S. Pat. No. 7,314,849 (B2), which is incorporated herein by reference in its entirety. Exemplary uses of the compound of the formula (I) include controlling undesirable vegetation, including grass, broadleaf and sedge weeds, in multiple non-crop and cropping situations.

As used herein, the sulfonylaminocarbonyltriazolinone herbicides inhibit the acetolactate synthetase enzyme, i.e., they act by inhibiting biosynthesis of the essential amino acids leucine, valine and isoleucine, thereby stopping cell division and plant growth. Sulfonylaminocarbonyltriazolinones include, but are not limited to flucarbazone, propoxycarbazone, thiencarbazone, and salts or esters thereof.

As used herein, flucarbazone is 4,5-dihydro-3-methoxy-4-methyl-5-oxo-N-[[2-(trifluoromethoxy)phenyl]sulfonyl]-1H-1,2,4-triazole-1-carboxamide and has the following structure:

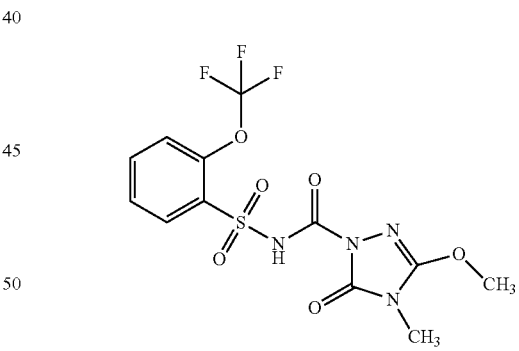

Flucarbazone's herbicidal activity is exemplified in *The Pesticide Manual*, Fifteenth Edition, 2009. Flucarbazone provides post-emergence control of annual grass weeds and some perennial grass weeds and some broad-leaved weeds.

As used herein, propoxycarbazone is methyl 2-[[[(4,5-dihydro-4-methyl-5-oxo-3-propoxy-1H-1,2,4-triazol-1-yl)-carbonyl]amino]sulfonyl]benzoate and has the following structure:

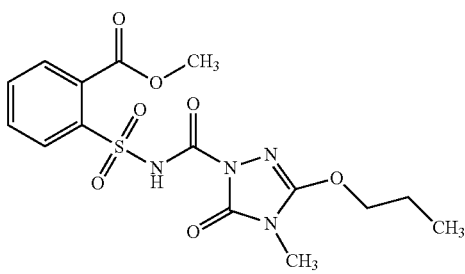 [SMILES: CCCOc1nn(C(=O)NS(=O)(=O)c2ccccc2C(=O)OC)c(=O)n1C]

Propoxycarbazone's herbicidal activity is exemplified in *The Pesticide Manual*, Fifteenth Edition, 2009. Propoxycarbazone provides post-emergence control of grass weeds and some broad-leaved weeds.

As used herein, thiencarbazone is 4-[[[(4,5-dihydro-3-methoxy-4-methyl-5-oxo-1H-1,2,4-triazol-1-yl)carbonyl]amino]sulfonyl]-5-methyl-3-thiophenecarboxylic acid and has the following structure:

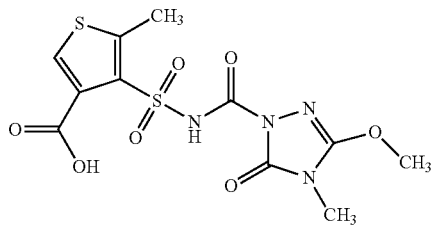 [SMILES: COc1nn(C(=O)NS(=O)(=O)c2c(C(=O)O)csc2C)c(=O)n1C]

Thiencarbazone's herbicidal activity is exemplified in *The Pesticide Manual*, Fifteenth Edition, 2009. Thiencarbazone provides post-emergence control of grass weeds and some broad-leaved weeds.

As used herein, herbicide means an active ingredient that kills, controls or otherwise adversely modifies the growth of plants.

As used herein, a herbicidally effective or vegetation controlling amount is an amount of active ingredient which causes an adversely modifying effect and includes deviations from natural development, killing, regulation, desiccation, retardation, and the like.

As used herein, controlling undesirable vegetation means preventing, reducing, killing, or otherwise adversely modifying the development of plants and vegetation. Described herein are methods of controlling undesirable vegetation through the application of certain herbicide combinations or compositions. Methods of application include, but are not limited to applications to the vegetation or locus thereof, as well as preemergence, postemergence, and foliar applications.

As used herein, plants and vegetation include, but are not limited to, germinant seeds, emerging seedlings, plants emerging from vegetative propagules, and established vegetation.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can by hydrolyzed, oxidized, metabolized, or otherwise converted, e.g., in plants, water, or soil, to the corresponding carboxylic acid which, depending on the pH, may be in the dissociated or undissociated form. Exemplary salts include those derived from alkali or alkaline earth metals and those derived from ammonia and amines. Exemplary cations include sodium, potassium, magnesium, and aminium cations of the formula:

$$R^1R^2R^3R^4N^+$$

wherein $R^1$, $R^2$, $R^3$ and $R^4$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

Compositions and Methods

Provided herein are herbicidal compositions comprising a herbicidally effective amount of (a) a compound of the formula (I)

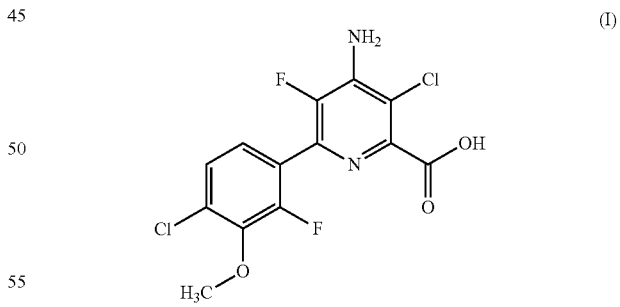

or an agriculturally acceptable salt or ester of thereof, and (b) a sulfonylaminocarbonyltriazone herbicide, or an agriculturally acceptable salt or ester thereof.

Provided herein also are methods of controlling undesirable vegetation comprising contacting the vegetation or applying to the soil or water adjacent thereto to prevent the emergence or growth of vegetation a herbicidally effective amount of the compound of formula (I) and (b) a sulfonylaminocarbonyltriazone herbicide, or an agriculturally acceptable salt or ester thereof. The undesirable vegetation can be immature undesirable vegetation. In certain embodiments, the methods employ the compositions described herein.

Furthermore, the combination of compound (I) or agriculturally acceptable salt or ester thereof and a sulfonylaminocarbonyltriazone herbicide, or an agriculturally acceptable salt or ester thereof can exhibit synergism, i.e., the herbicidal active ingredients are more effective in combination than when applied individually. The *Herbicide Handbook* of the Weed Science Society of America, Ninth Edition, 2007, p. 429 notes that "'synergism' [is] an interaction of two or more factors such that the effect when combined is greater than the predicted effect based on the response of each factor applied separately." Certain compositions described herein exhibit synergy as determined by the Colby's equation. Colby, S. R., *Calculation of the synergistic and antagonistic response of herbicide combinations*, Weeds 15:20-22, 1967.

The compound of formula (I) or an agriculturally acceptable salt or ester thereof and a sulfonylaminocarbonyltriazone herbicide, or an agriculturally acceptable salt or ester thereof, e.g., flucarbazone, propoxycarbazone, thiencarbazone, or an agriculturally acceptable salt or ester thereof, can be formulated in one composition, tank mixed, applied simultaneously, or applied sequentially.

Herbicidal activity is exhibited by the compounds when they are applied directly to the plant or to the soil or water adjacent the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. The compositions described herein can be applied as a post-emergence application, pre-emergence application, or in-water application to flooded paddy rice or water bodies (e.g., ponds, lakes and streams). Additionally, the compositions described herein can be applied to relatively immature undesirable vegetation to achieve the maximum control of weeds.

The compositions and methods provided herein can be used to control weeds in crops, including but not limited to cereal crops, direct-seeded, water-seeded and transplanted rice, wheat, durum, barley, oats, rye, sorghum, triticale, corn/maize, soybean, cotton, canola, oilseed rape, pastures, grasslands, rangelands, fallowland, turf, tree and vine orchards, aquatics, and IVM, and also in glyphosate, glufosinate, dicamba, imidazolinone, phenoxy auxin, 2,4-D, pyridyloxy auxin, aryloxyphenoxypropionate, acetyl CoA carboxylase (ACCase), acetolactate synthase (ALS), 4-hydroxyphenylpyruvate dioxygenase (HPPD, protoporphyrinogen oxidase (PPO), triazine, and bromoxynil tolerant crops (such as, but not limited to, soybean, cotton, canola/oilseed rape, rice, cereals, corn, turf, etc).

The compositions and methods provided herein can be used to control undesirable vegetation consisting of grass, broadleaf and sedge weeds. For example, the compositions and methods provided herein can be used to control undesirable vegetation such as *Alopecurus, Bromus, Apera, Phalaris, Lolium, Avena, Setaria, Pennisetum, Poa,* and *Echinochloa*; broadleaf weeds such as *Papaver, Galium, Lamium, Kochia, Salsola, Matricaria, Veronica, Viola, Capsella, Descurainia, Cirsium, Polygonum, Sinapis, Chenopodium, Amaranthus, Aeschynomene, Sesbania, Centaurea, Stellaria, Anthemis, Brassica, Raphanus, Euphorbia, Rapistrum, Convolvulus,* *Sonchus, Geranium, Portulaca, Malva, Silene,* and *Monochoria*; and sedge species such as *Cyperus* and *Scirpus*.

For further example, the combination of compound (I) or agriculturally acceptable ester or salt thereof and a sulfonylaminocarbonyltriazone herbicide, or an agriculturally acceptable salt or ester thereofcan be used to control chickweed (*Stellaria media* L; STEME), scented mayweed (*Matricaria chamomila* L; MATCH), Canada thistle (*Cirsium arvense* L; CIRAR), bird's-eye speedwell (*Veronica persica* L; VERPE), purple deadnettle (*Lamium purpureum* L; LAMPU).

In the compounds and methods described herein, an agriculturally acceptable ester or salt of compound (I) is employed. An agriculturally acceptable ester, such as an aralkyl or alkyl ester, can be employed. The ester can be a $C_{1-4}$ alkyl ester, a n-butyl ester, a benzyl ester, or a substituted benzyl ester. Additionally, the carboxylic acid form of compound (I) or the carboxylate salt of the compound of formula (I) can be used.

In the compounds and methods described herein, an agriculturally acceptable ester or salt of a sulfonylaminocarbonyltriazone herbicide, e.g., flucarbazone, propoxycarbazone, thiencarbazone, or a salt or ester thereof, can be used. For example, the sodium salt of flucarbazone, propoxycarbazone, or thiencarbazone can be used.

For example, the compound of formula (I) or an agriculturally acceptable benzyl ester can be combined with flucarbazone or a salt or ester thereof. For further example, the compound of formula (I) or an agriculturally acceptable benzyl ester can be combined with propoxycarbazone or a salt or ester thereof.

In the compositions and methods described herein, the weight ratio of the compound of formula (I) or salt or ester thereof to the sulfonylaminocarbonyltriazone herbicide is within the range of from 5:1 to 1:256. The weight ratio of the compound of formula (I) or salt or ester thereof to the sulfonylaminocarbonyltriazone herbicide also can be within the range of from 5:1 to 1:128, 5:1 to 1:64, 5:1 to 1:32, 5:1 to 1:24, 5:1 to 1:16, 5:1 to 1:14, 5:1 to 1:12, 5:1 to 1:10, 5:1 to 1:9, 5:1 to 1:8, 5:1 to 1:7, 5:1 to 1:6, 5:1 to 1:5, 5:1 to 1:4, 5:1 to 1:3, 5:1 to 1:2, or 5:1 to 1:1. Additionally, the weight ratio of the compound of formula (I) or salt or ester thereof to the sulfonylaminocarbonyltriazone herbicide can be within the range of from 2:1 to 1:128, 2:1 to 1:64, 2:1 to 1:32, 2:1 to 1:24, 2:1 to 1:16, 2:1 to 1:14, 2:1 to 1:12, 2:1 to 1:10, 2:1 to 1:9, 2:1 to 1:8, 2:1 to 1:7, 2:1 to 1:6, 2:1 to 1:5, 2:1 to 1:4, 2:1 to 1:3, 2:1 to 1:2, or 2:1 to 1:1. Further, the weight ratio of the compound of formula (I) or salt or ester thereof to the sulfonylaminocarbonyltriazone herbicide can be within the range of from 1.9:1 to 1:2, 1.8:1 to 1:2, 1.7:1 to 1:2, 1.6:1 to 1:2, 1.5:1 to 1:2, 1.4:1 to 1:2, 1.3:1 to 1:2, 1.2:1 to 1:2, 1.1:1 to 1:2, 1:1 to 1:2, 2:1 to 1:1.9, 2:1 to 1:1.8, 2:1 to 1:1.7, 2:1 to 1:1.6, 2:1 to 1:1.5, 2:1 to 1:1.4, 2:1 to 1:1.3, 2:1 to 1:1.2, or 2:1 to 1:1.1. Additionally, the weight ratio of the compound of formula (I) or salt or ester thereof to the sulfonylaminocarbonyltriazone herbicide can be 1:1, 1:2, 2:1, 1:3, 3:1, 1:4, 4:1, 1:5, 5:1, 9:8, or 9:15.

The application rate will depend upon the particular type of weed to be controlled, the degree of control required, and the timing and method of application. In general, the compositions as described herein can be applied at an application rate of from 4 grams acid equivalent per hectare (g ae/ha) to 1200 g ae/ha based on the total amount of active ingredients in the composition. The composition as described herein also can be applied at an application rate of from 4 g ae/ha to 1000 g ae/ha, 4 g ae/ha to 800 g ae/ha, 4 g ae/ha to 600 g ae/ha, 4 g ae/ha to 500 g ae/ha, 4 g ae/ha to 400 g ae/ha, 4 g ae/ha to 300 g ae/ha, 4 g ae/ha to 250 g ae/ha, 4 g ae/ha to 200 g ae/ha, 4 g ae/ha to 150 g ae/ha, 4 g ae/ha to 100 g ae/ha, 4 g ae/ha to 90 g ae/ha, 4 g ae/ha to 80 g ae/ha, 4 g ae/ha to 70 g ae/ha, 4 g ae/ha to 60 g ae/ha, 4 g ae/ha to 50 g ae/ha, 4 g ae/ha to 40 g ae/ha, 4 g ae/ha to 30 g ae/ha, or 4 g ae/ha to 20 g ae/ha, 4 g ae/ha to 10 g ae/ha, 4 g ae/ha to 5 g ae/ha, or 4 g ae/ha based on the total amount of active ingredients in the composition.

The components of the mixtures described herein can be applied either separately or as part of a multipart herbicidal system.

The mixtures described herein can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the compositions and methods described herein include, but are not limited to: 4-CPA; 4-CPB; 4-CPP; 2,4-D; 2,4-D choline salt, 2,4-D esters and amines, 2,4-DB; 3,4-DA; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, B CPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, flurtamone, fluthiacet, fomesafen, foramsulfuron, fosamine, fumiclorac, furyloxyfen, glufosinate, glufosinate-ammonium, glufosinate-P-ammonium, glyphosate, halosafen, halosulfuron-methyl, haloxydine, haloxyfop-methyl, haloxyfop-P-methyl, hexachloroacetone, hexaflurate, hexazinone, imazamethabenz, imazamox, imazapic, imazapyr, imazaquin, imazosulfuron, imazethapyr, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, metsulfuron-methyl, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, orthodichlorobenzene, orthosulfamuron, oryzalin, oxadiargyl, oxadiazon, oxapyrazon, oxasulfuron, oxaziclomefone, oxyfluorfen, paraflufen-ethyl, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen-ethyl, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-sodium, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thifensulfurn-methyl, thiobencarb, tiocarbazil, tioclorim, topramezone, tralkoxydim, triafamone, tri-allate, triasulfuron, triaziflam, tribenuron, tribenuron-methyl, tricamba, triclopyr choline salt, triclopyr esters and salts, tridiphane, trietazine, trifloxysulfuron, trifluralin, triflusulfuron, trifop, trifopsime, trihydroxytriazine, trimeturon, tripropindan, tritac tritosulfuron, vernolate, xylachlor and salts, esters, optically active isomers and mixtures thereof.

The compositions and methods described herein also can be used in conjunction with glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, and bromoxynil on glyphosate-tolerant, glufosinate-tolerant, dicamba-tolerant, phenoxy auxin-tolerant, pyridyloxy auxin-tolerant, aryloxyphenoxypropionate-tolerant, ACCase-tolerant, imidazolinone-tolerant, ALS-tolerant, HPPD-tolerant, PPO-tolerant, triazine-tolerant, bromoxynil-tolerant, and crops possessing multiple or stacked traits conferring tolerance to multiple chemistries and/or multiple modes of action. The compound of formula (I) or salt or ester thereof and complementary herbicide or salt or ester thereof can be used in combination with herbicides that are selective for the crop being treated and which complement the spectrum of weeds controlled by these compounds at the application rate employed. The compositions described herein and other complementary herbicides can be applied at the same time, either as a combination formulation or as a tank mix.

The compositions described herein can be employed in combination with one or more herbicide safeners, such as AD-67 (MON 4660), benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, jiecaowan, jiecaoxi, mefenpyr-diethyl, mephenate, naphthalic anhydride (NA), oxabetrinil, R29148 and N-phenyl-sulfonylbenzoic acid amides, to enhance their selectivity. The safener can be cloquintocet or an ester or salt thereof, such as cloquintocet (mexyl). Cloquintocet can be used to antagonize harmful effects of the compositions on rice and cereals.

The compositions provided herein can further include at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank mixed.

Suitable agricultural adjuvants and carriers include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water can be the carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

The compositions described herein further can include one or more surface-active agents. Such surface-active agents are employed in both solid and liquid compositions, and in certain embodiments those designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, and in certain embodiments, methyl esters.

These materials, such as vegetable or seed oils and their esters, can be used interchangeably as an agricultural adjuvant, as a liquid carrier or as a surface active agent.

Other exemplary additives for use in the compositions provided herein include but are not limited to compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of active ingredients in the compositions described herein is generally from 0.0005 to 98 percent by weight. Additionally, concentration is from 0.0006 to 90 percent by weight can be used. In compositions designed to be employed as concentrates, the active ingredients, can be present in a concentration from 0.1 to 98 weight percent, or from 0.5 to 90 weight percent. Such compositions can be diluted with an inert carrier, such as, for example, water, before application. The diluted compositions usually applied to vegetation or the soil or water adjacent thereto can contain from 0.0006 to 15.0 weight percent active ingredient or from 0.001 to 10.0 weight percent.

The present compositions can be applied to weeds or to the soil or water adjacent the weeds by use of conventional ground or aerial dusters, sprayers, and granule applicators, by addition to irrigation or paddy water, and by other conventional means known to those skilled in the art.

The described compositions and methods and following examples are for illustrative purposes and are not intended to limit the scope of the claims. Other modifications, uses, or combinations with respect to the compositions and methods described herein will be apparent to a person of ordinary skill in the art without departing from the spirit and scope of the claimed subject matter.

EXAMPLES

Evaluation of Postemergence Herbicidal Activity of Mixtures in Cereal Crops

Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days in a greenhouse with an approximate 14 hour photoperiod which was maintained at about 18° C. during the day and 17° C. during the night. Nutrients and water were added on a regular basis and supplemental lighting was provided with overhead metal halide 1000-Watt lamps as necessary. The plants were employed for testing when they reached the second or third true leaf stage.

Treatments consisted of the benzyl ester of the compound of formula (I) (Compound A as listed in Tables 1-8) and a second cereal herbicide alone and in combination. Specifically, weighed amounts of Compound A (the benzyl ester of 4-amino-3-chloro-5-fluoro-6-(4-chloro-2-fluoro-3-methoxyphenyl)pyridine-2-carboxylic acid) were placed in 25 milliliter (mL) glass vials and dissolved in a volume of 97:3 v/v acetone/DMSO to obtain 4.5 milligrams (mg) active ingredient (ai)/mL stock solutions. If the experimental compound did not dissolve readily, the mixture was warmed and/or sonicated. The concentrated stock solutions were diluted to 1.5 mg ai/mL with the addition of 2 volumes of an aqueous mixture containing acetone, water, isopropyl alcohol, DMSO, Agri-dex crop oil concentrate, and Triton® X-77 surfactant in a 64.7:26.0:6.7:2.0:0.7:0.01 v/v ratio. A dilution solution was prepared by mixing 1 volume of 97:3 v/v acetone/DMSO and 2 volumes of an aqueous mixture containing acetone, water, isopropyl alcohol, DMSO, Agri-dex crop oil concentrate, and Triton® X-77 surfactant in a 64.7:26.0:6.7:2.0:0.7:0.01 v/v ratio. Compound requirements are based upon a 12 mL application volume at a rate of 187 liters per hectare (L/ha). Spray solutions of the second cereal herbicide and experimental compound mixtures were prepared by adding the stock solutions to the appropriate amount of dilution solution to form 12 mL spray solution with active ingredients in two- and three-way combinations. Formulated compounds were applied to the plant material with an overhead Mandel track sprayer equipped with 8002E nozzles calibrated to deliver 187 L/ha over an application area of 0.503 square meters ($m^2$) at a spray height of 18 inches (43 cm) above average plant canopy. Control plants were sprayed in the same manner with the solvent blank.

The treated plants and control plants were placed in a greenhouse as described above and watered by sub-irrigation to prevent wash-off of the test compounds. After 20-22 days, the condition of the test plants as compared with that of the control plants was determined visually and scored on a scale of 0 to 100 percent where 0 corresponds to no injury and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.). Specifically, the following equation was used to calculate the expected activity of mixtures containing two active ingredients, A and B:

Expected=$A+B-(A \times B/100)$

A=observed efficacy of active ingredient A at the same concentration as used in the mixture.

B=observed efficacy of active ingredient B at the same concentration as used in the mixture.

Details of the compounds tested, application rates employed, plant species tested, and results are given in Table 1, Table 2, Table 3, Table 4, Table 5, Table 6, Table 7, and Table 8.

TABLE 1

Synergistic Activity of Foliar-Applied Compound A Benzyl ester and Flucarbazone-sodium Herbicidal Compositions on Weed Control in a Cereal Cropping System

| Application Rate (g/ha) | | VERPE | | STEME | | MATCH | | CIRAR | |
|---|---|---|---|---|---|---|---|---|---|
| Compound A | Flucarbazone-Na | Obs | Exp | Obs | Exp | Obs | Exp | Obs | Exp |
| 8.75 | 0 | 50 | — | 68 | — | 20 | — | 40 | — |
| 0 | 7.5 | 0 | — | 60 | — | 30 | — | 50 | — |
| 8.75 | 7.5 | 55 | 50 | 93 | 87 | 63 | 44 | 78 | 70 |

VERPE = *Veronica persica*
STEME = *Stellaria media*
MATCH = *Matricaria chamomila*
CIRAR = *Cirsium arvense*

TABLE 2

Synergistic Activity of Foliar-Applied Compound A Benzyl ester and Flucarbazone-sodium Herbicidal Compositions on Weed Control in a Cereal Cropping System

| Application Rate (g/ha) | | ALOMY | | APESV | | LOLMG | |
|---|---|---|---|---|---|---|---|
| Compound A | Flucarbazone-Na | Obs | Exp | Obs | Exp | Obs | Exp |
| 5 | 0 | 0 | — | 0 | — | 0 | — |
| 10 | 0 | 0 | — | 0 | — | 0 | — |
| 0 | 3.75 | 8 | — | 33 | — | 0 | — |
| 0 | 7.5 | 17 | — | 75 | — | 0 | — |
| 5 | 3.75 | 18 | 8 | 52 | 33 | 0 | 0 |
| 10 | 3.75 | 23 | 8 | 48 | 33 | 7 | 0 |
| 5 | 7.5 | 13 | 17 | 73 | 75 | 57 | 0 |
| 10 | 7.5 | 17 | 17 | 85 | 75 | 37 | 0 |

ALOMY = *Alopecurus myosuroides*
APESV = *Apera spica-venti*
LOLMG = *Lolium multiflorum subsp. gaudini*

TABLE 3

Synergistic Activity of Foliar-Applied Compound A Benzyl ester and Flucarbazone-sodium Herbicidal Compositions on Weed Control in a Cereal Cropping System

| Application Rate (g ai/ha) | | TRZAW | | STEME | | PAPRH | | SASKR | | MATCH | | VERPE | | VIOTR | |
|---|---|---|---|---|---|---|---|---|---|---|---|---|---|---|---|
| Compound A | Flucarbazone-Na | Obs | Exp | Obs | Exp | Obs | Exp | Obs | Exp | Obs | Exp | Obs | Exp | Obs | Exp |
| 5 | 0 | 7 | — | 50 | — | 46 | — | 75 | — | 20 | — | 13 | — | 27 | — |
| 10 | 0 | 7 | — | 63 | — | 48 | — | 78 | — | 40 | — | 25 | — | 37 | — |
| 0 | 3.75 | 2 | — | 3 | — | 0 | — | 10 | — | 10 | — | 0 | — | 7 | — |
| 0 | 7.5 | 7 | — | 7 | — | 0 | — | 0 | — | 10 | — | 0 | — | 7 | — |
| 5 | 3.75 | 5 | 8 | 55 | 52 | 20 | 46 | 87 | 78 | 30 | 28 | 17 | 13 | 23 | 32 |
| 10 | 3.75 | 12 | 8 | 73 | 65 | 78 | 48 | 92 | 81 | 60 | 46 | | | | |
| 5 | 7.5 | 12 | 13 | 58 | 53 | 53 | 46 | 87 | 77 | 50 | 28 | 30 | 13 | 55 | 32 |
| 10 | 7.5 | 10 | 13 | 91 | 66 | 77 | 48 | 87 | 80 | 79 | 46 | 30 | 25 | 55 | 41 |

TRZAW = *Triticum aestivum*
STEME = *Stellaria media*
PAPRH = *Papaver rhoeas*
SASKR = *Alopecurus myosuroides*
MATCH = *Apera spica-venti*
VERPE = *Veronica persica*
VIOTR = *Viola tricolor*

TABLE 4

Synergistic Activity of Foliar-Applied Compound A Benzyl ester and Propoxycarbazone-sodium Herbicidal Compositions on Weed Control in a Cereal Cropping System

| Application Rate (g/ha) | | LAMPU | | STEME | | CIRAR | |
|---|---|---|---|---|---|---|---|
| Compound A | Propoxycarbazone-Na | Obs | Exp | Obs | Exp | Obs | Exp |
| 8.75 | 0 | 83 | — | 68 | — | 40 | — |
| 0 | 15 | 0 | — | 45 | — | 65 | — |
| 8.75 | 15 | 93 | 83 | 90 | 82 | 95 | 79 |

LAMPU = *Lamium purpureum*
STEME = *Stellaria media*
CIRAR = *Cirsium arvense*

TABLE 5

Synergistic Activity of Foliar-Applied Compound A Benzyl ester and Propoxycarbazone-sodium Herbicidal Compositions on Weed Control in a Cereal Cropping System

| Application Rate (g ha) | | ALOMY | | APESV | | SETVI | | LOLMG | |
|---|---|---|---|---|---|---|---|---|---|
| Compound A | Propoxycarbazone-Na | Obs | Exp | Obs | Exp | Obs | Exp | Obs | Exp |
| 5 | 0 | 0 | — | 0 | — | 0 | — | 0 | — |
| 10 | 0 | 0 | — | 0 | — | 0 | — | 0 | — |
| 0 | 7.5 | 10 | — | 17 | — | 0 | — | 3 | — |
| 0 | 15 | 43 | — | 23 | — | 0 | — | 20 | — |
| 5 | 7.5 | 15 | 10 | 22 | 17 | 13 | 0 | 7 | 3 |
| 10 | 7.5 | 15 | 10 | 27 | 17 | 23 | 0 | 13 | 3 |
| 5 | 15 | 47 | 43 | 22 | 23 | 20 | 0 | 13 | 20 |
| 10 | 15 | 50 | 43 | 32 | 23 | 33 | 0 | 20 | 20 |

ALOMY = *Alopecurus myosuroides*
APESV = *Apera spica-venti*
LOLMG = *Lolium multiflorum subsp. gaudini*
SETVI = *Setaria viridis*

TABLE 6

Synergistic Activity of Foliar-Applied Compound A Benzyl ester and Propoxycarbazone-sodium Herbicidal Compositions on Weed Control in a Cereal Cropping System

| Application Rate (g ai/ha) | | TRZAW | | STEME | | PAPRH | | KCHSC | | MATCH | | VIOTR | |
|---|---|---|---|---|---|---|---|---|---|---|---|---|---|
| Compound A | Propoxycarbazone-Na | Obs | Exp | Obs | Exp | Obs | Exp | Obs | Exp | Obs | Exp | Obs | Exp |
| 5 | 0 | 7 | — | 50 | — | 46 | — | 60 | — | 20 | — | 27 | — |
| 10 | 0 | 7 | — | 63 | — | 48 | — | 57 | — | 40 | — | 37 | — |
| 0 | 7.5 | 8 | — | 12 | — | 18 | — | 13 | — | 13 | — | 13 | — |
| 0 | 15 | 5 | — | 10 | — | 23 | — | 25 | — | 20 | — | 23 | — |
| 5 | 7.5 | 8 | 14 | 73 | 56 | 75 | 55 | 75 | 65 | 88 | 30 | 63 | 36 |
| 10 | 7.5 | 12 | 14 | 80 | 68 | 85 | 58 | 78 | 62 | 94 | 48 | 65 | 45 |
| 5 | 15 | 10 | 11 | 67 | 55 | 73 | 58 | 63 | 70 | 93 | 36 | 60 | 44 |
| 10 | 15 | 10 | 11 | 80 | 67 | 80 | 60 | 79 | 68 | 85 | 52 | 68 | 51 |

TRZAW = *Triticum aestivum*
STEME = *Stellaria media*
PAPRH = *Papaver rhoeas*
KCHSC = *Kochia scoparia*
MATCH = *Apera spica-venti*
VIOTR = *Viola tricolor*

TABLE 7

Synergistic Activity of Foliar-Applied Compound A Benzyl ester and Thiencarbazone-methyl Herbicidal Compositions on Weed Control in a Cereal Cropping System

| Application Rate (g ha) | | TRZAS | | HORVS | | LAMPU | | GALAP | | CHEAL | |
|---|---|---|---|---|---|---|---|---|---|---|---|
| Compound A | Thiencarbazone-methyl | Obs | Exp | Obs | Exp | Obs | Exp | Obs | Exp | Obs | Exp |
| 2.5 | 0 | 0 | — | 0 | — | 80 | — | 60 | — | 50 | — |
| 5 | 0 | 5 | — | 0 | — | 80 | — | 60 | — | 60 | — |
| 0 | 2.5 | 0 | — | 0 | — | 10 | — | 20 | — | 10 | — |
| 2.5 | 2.5 | 0 | 0 | 0 | 0 | 90 | 68 | 90 | 68 | 70 | 55 |
| 5 | 2.5 | 0 | 5 | 0 | 0 | 95 | 68 | 98 | 68 | 80 | 64 |

TRZAS = *Triticum aestivum*
HORVS = *Hordeum vulgare*
LAMPU = *Lamium purpureum*
GALAP = *Galium aparine*
CHEAL = *Chenopodium album*

TABLE 8

Synergistic Activity of Foliar-Applied Compound A Benzyl ester and Thiencarbazone-methyl Herbicidal Compositions on Weed Control in a Cereal Cropping System

| Application Rate (g ha) | | KCHSC | | SASKR | | VIOTR | | MATCH | | CIRAR | |
|---|---|---|---|---|---|---|---|---|---|---|---|
| Compound A | Thiencarbazone-methyl | Obs | Exp | Obs | Exp | Obs | Exp | Obs | Exp | Obs | Exp |
| 2.5 | 0 | 20 | — | 10 | — | 10 | — | 0 | — | 10 | — |
| 5 | 0 | 40 | — | 60 | — | 10 | — | 10 | — | 20 | — |
| 0 | 2.5 | 0 | — | 10 | — | 10 | — | 10 | — | 0 | — |
| 2.5 | 2.5 | 70 | 20 | 70 | 19 | 70 | 19 | 90 | 10 | 30 | 10 |
| 5 | 2.5 | 65 | 40 | 80 | 64 | 60 | 19 | 80 | 19 | 40 | 20 |

KCHSC = *Kochia scoparia* (L.) Schrad.
SASKR = *Salsola tragus*
VIOTR = *Viola tricolor*
MATCH = *Matricaria chamomila*
CIRAR = *Cirsium arvense*

What is claimed is:

1. A synergistic herbicidal composition comprising a herbicidally effective amount of (a) an agriculturally acceptable benzyl ester of a compound of the formula (I)

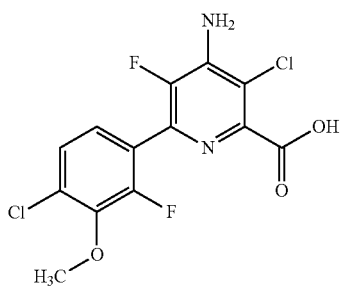

(I)

and (b) a sulfonylaminocarbonyltriazone herbicide, or an agriculturally acceptable salt or ester thereof, wherein the weight ratio of the agriculturally acceptable benzyl ester of the compound of the formula (I) to the sulfonylaminocarbonyltriazone herbicide, or an agriculturally acceptable salt or ester thereof is from 5:1 to about 1:5.

2. The composition of claim 1, wherein the sulfonylaminocarbonyltriazone herbicide is flucarbazone, propoxycarbazone, thiencarbazone, or a salt or ester thereof.

3. The composition of claim 1, wherein (b) is flucarbazone or a salt or ester thereof.

4. The composition of claim 1, wherein (b) is propoxycarbazone or a salt or ester thereof.

5. The composition of claim 1, further comprising a herbicide safener.

6. The composition of claim 1, further comprising an agriculturally acceptable adjuvant or carrier.

7. The composition of claim 1, which is synergistic as wherein synergy is determined by the Colby equation.

8. A method of controlling undesirable vegetation comprising contacting the undesirable vegetation or applying to the soil or water adjacent thereto with the composition of claim 1.

9. The method of claim 8, wherein the undesirable vegetation is controlled in cereal crops.

10. The method of claim 8, wherein the undesirable vegetation is controlled in direct-seeded rice, water-seeded rice, transplanted rice, wheat, barley, oats, rye, sorghum, corn or maize, soybean, cotton, canola, oilseed rape, pastures, grasslands, rangelands, fallowland, turf, tree and vine orchards, aquatics, or IVM.

11. The method of claim 8, wherein the undesirable vegetation is controlled in glyphosate, glufosinate, dicamba, imidazolinone, 2,4-D, ALS, or ACC'ase tolerant crops.

12. The method of claim 8, wherein the contacting is a post-emergence application, pre-emergence application, or in-water application to flooded paddy rice or water bodies.

13. The method of claim 8, wherein the undesirable vegetation is immature undesirable vegetation.

* * * * *